United States Patent [19]

Therre et al.

[11] Patent Number: 5,461,174
[45] Date of Patent: Oct. 24, 1995

[54] METHOD OF REACTING CARBOXYLIC CHLORIDES DISSOLVED IN CARBOXYLATES

[75] Inventors: Joerg Therre, Worms, Germany; Hans V. Schwarz, Waterloo, Belgium; David Agar, Mannheim, Germany

[73] Assignee: BASF Aktiengesellschaft, Ludwigshafen

[21] Appl. No.: 249,591

[22] Filed: May 26, 1994

[51] Int. Cl.⁶ .................................................. C07C 67/08
[52] U.S. Cl. ............................................. 560/98; 560/96
[58] Field of Search ........................................ 560/96, 98

[56] References Cited

U.S. PATENT DOCUMENTS 2,623,034  12/1952  Flory .
4,379,912  4/1983  Lu .

FOREIGN PATENT DOCUMENTS 1292655  3/1966  European Pat. Off. .
1476755  of 0000  France .

OTHER PUBLICATIONS

Z. Org. Chim 1 (1965) No. 8 pp. 1396–1399.
Houben–Weyl, 4th Edition (1952) vol. VIII, pp. 545–547.
Journal of Pharmaceutical Sciences, vol. 56, No. 11 (1967) p. 1448.

*Primary Examiner*—José G. Dees
*Assistant Examiner*—Samuel Barts
*Attorney, Agent, or Firm*—Mary E. Golota

[57]  ABSTRACT

The invention relates to a method of reacting alkyl carboxylate chlorides and/or carboxylic dichlorides dissolved in corresponding dialkyl carboxylates with the corresponding alkanol at temperatures ranging from 60° to 300° C., in which the resultant hydrogen chloride remains in the reaction mixture.

6 Claims, No Drawings

METHOD OF REACTING CARBOXYLIC CHLORIDES DISSOLVED IN CARBOXYLATES

The invention relates to a method of reacting carboxylic chlorides dissolved in carboxylates which are particularly useful for working up carboxylic acid diesters used as solvents during the preparation of isocyanates by phosgenation of amines.

The preparation of isocyanates and especially di- or poly-isocyanates by the reaction of the corresponding amines with phosgene is well known and has been described in the literature in a number of places. To carry out the process, usually both the amine and the phosgene are dissolved in a solvent and caused to react with each other. For example, particularly aromatic, optionally halogenated hydrocarbons such as toluene or chlorobenzenes can be used as solvents. The use of alkyl carboxylates as solvents for the phosgenation of amines is also possible. Preference should be given here to aromatic esters, since these are essentially chemically inert under the reaction conditions used.

For example, FR-A 1,476,755 describes the use of alkyl isophthalates as solvents when reacting toluylenediamine with phosgene to form toluylenediisocyanate. Alkyl carboxylate chlorides as well as, to a minor degree, carboxylic dichlorides are formed during the phosgenation reaction on account of the action of phosgene and/or hydrogen chloride on the solvent. This causes losses of solvent, which in turn effects an increase in the cost of the process.

Since these reaction products remain in the solvent when the reaction mixture is purified by distillation, they are entrained with the solvents and accumulate therein. They can amount to as much as 40 % of the solvent. In this case, the acid chlorides react with the starting product toluylenediamine, which leads to a decrease in the yield produced by the process. These reaction products may be deposited in the plant and thus lead to breakdowns in the plant. Since removal of the acid chlorides by distillation is not possible, they must be removed from the reaction mixture in some other suitable manner, most advantageously by the reverse reaction to form the corresponding esters.

The prior art provides a series of proposals for the conversion of carboxylic chlorides to carboxylates. *Z. Org. Chim.* 1 (1965) No. 8, pp. 1396–1399, suggests that alkyl terephthalate chloride be caused to react with mercury diacetaldehyde in the presence of pyridine to produce vinyl alkyl terephthalate. The disadvantage of this process is the necessity to use a mercury derivative as well as the auxiliary pyridine.

It is well known that it is possible to react acid chlorides with alcohols to form esters. The relevant literature expresses the opinion, however, that auxiliaries and/or solvents are necessary for the reaction of aromatic carboxylic chlorides with alcohols, and that the resultant hydrogen chloride must be removed from the reaction mixture by the addition of hydrogen chloride-binding agents such as bases, in particular pyridine, or by passing through nitrogen or making use of vacuum. This makes the prior processes very expensive, and they have long reaction times and give poor yields, and are thus unsuitable for the purification of the carboxylate used as solvent for isocyanate synthesis.

Thus *Houben-Weyl*, 4th Edition (1952), Vol. VIII, pp. 545–547, describes a number of possibilities for carrying out the reaction of an acid chloride with an alcohol in the presence of hydrogen chloride-binding auxiliaries such as bases or pyridine. This usually involves, however, the loss of the hydrogen chloride-binding auxiliary as well as the necessity to remove the resultant reaction products from the reaction mixture.

DE-A12 92655 proposes, on account of the inertness of the aromatic acid chlorides, a method of removing the resultant hydrogen chloride from the equilibrium mixture by the use of acid-binding agents, or a method of carrying out the reaction in a polar halohydrocarbon as solvent. This solvent must be removed by distillation following completion of the reaction.

*Journal of Pharmaceutical Sciences*, Vol. 56, No. 11 (1967), pp. 1448, recommends, in a general set of directions, that an aromatic carboxylic dichloride be refluxed with an alcohol for from 4 to 6 h. The drawbacks of the process are the very long reaction time, the low yield of only 55 to 75% as well as the necessity to purify the end product by an expensive procedure.

*Journal für praktische Chemie*, 4th Edition, Vol. 27, pp. 236–238, describes the reaction of isophthalic dichloride with isopropanol, isobutanol, and isopentanol. The drawbacks of the process are a very high, six-fold excess of the alcohol, a reaction time of 10 hours and a yield of less than 37%.

In US-A4379912 carboxylic dichlorides are converted to esters at temperatures ranging from 180° to 220° C. in the presence of zinc acetate and antimony oxide. A disadvantage here is that the catalysts must be separated in a separate purification step.

US-A 2,623,034 relates to the preparation of crystalline tetramethylene/isophthalate polymers by the reaction of terephthalic dichloride with tetramethylene glycol, and proposes that the resultant hydrogen chloride be removed by purging with nitrogen or by the use of a vacuum. This process cannot be used when very volatile lower alkanols are used as the alcohol.

The processes described in the prior literature are thus encumbered with considerable drawbacks such as poor yield, slow reaction, and the use of catalysts, auxiliaries, or solvents. They are not suitable for the purification of carboxylic acid diesters used as phosgenation solvents.

It is an object of the present invention to provide a process for the conversion of carboxylic chlorides dissolved in dialkyl carboxylates, especially those based on aromatic carboxylic acids, to the corresponding dialkyl carboxylates, which avoids the drawbacks of the prior art. This object can be achieved, surprisingly, by a method of reacting an alkyl carboxylate chloride and/or carboxylic dichloride, dissolved in a corresponding dialkyl carboxylate, with the corresponding alkanol at temperatures ranging from 60° to 300° C. and preferably from 100° to 250° C., during which reaction the resulting hydrogen chloride remains in the reaction mixture.

Thus the invention relates to a method of reacting alkyl carboxylate chlorides and/or carboxylic dichlorides dissolved in corresponding dialkyl carboxylates with the corresponding alkanol at temperatures ranging from 60° to 300° C. and preferably from 100° to 250° C., during which reaction the resultant hydrogen chloride remains in the reaction mixture.

The reaction times are, depending, in particular, on the concentration of the carboxylic chloride in the dialkyl ester, from 1 second to 4 hours and preferably from 1 minute to 3 hours. The reaction is carried out by mixing the dialkyl carboxylate, which contains between 0.05 and 40 wt % of acid chlorides, based on the total weight, with the alcohol corresponding to the dialkyl carboxylate, heating the reaction mixture to the reaction temperature specified, leaving the reaction mixture at this temperature until the conversion of the acid chloride is complete, and then allowing the mixture to cool.

The reaction time ranges from 1 second to 4 hours depending on the concentration of the acid chloride and can be readily determined by preliminary tests.

The hydrogen chloride formed during the reaction remains in the reaction mixture over the entire reaction time. If quantative conversion is the target, it is necessary to adjust the molar ratio of acid chloride groups to alcohol to at least 1:1. The reaction is accelerated when the alcohol is used in excess. This excess should be from 0.005 mol/kg to 10 mol/kg and preferably from 0.05 mol/kg to 5 mol/kg.

Unconverted alcohol can be removed from the reaction mixture on completion of the reaction in any manner known per se, eg, by distillation or purging with an inert gas. A greater excess of alcohol than that stated has no adverse effect on the reaction, but due to the expense incurred by the removal of the unconverted alcohol the overall cost of the process would rise.

The hydrogen chloride formed during the reaction is also removed from the reaction mixture together with the unconverted alcohol. The alcohol can be predissolved in carboxylate prior to commencement of the reaction and then combined with the acid chloride-containing carboxylate. Alternatively, the alcohol can be used as pure substance.

The process makes it possible to complete the reaction between the acid chloride and the alcohol within a short time, frequently within only a few minutes. This means that only small-size apparatus is required. The reaction may be carried out continuously or batchwise. Both tubular reactors and stirred boilers are suitable apparatus. The pressure in the reaction vessel has no effect on the reaction. The process can be carried out under the pressure which establishes itself in the reaction vessel at the reaction temperature. This pressure is usually below 50 bar and frequently below 17 bar.

Except for said separation of excess alcohol, if required, it is unnecessary to purify the end product. The process of the invention can be used to particular advantage in the purification of dialkyl isophthalates used as solvents for the phosgenation of toluylenediamine to toluylenediisocyanate. All products with alkanols having from 1 bis 20 carbon atoms in the main chain in particular methyl, ethyl, propyl, butyl, octyl, and especially ethyl groups, may be used as dialkyl isophthalates.

The dialkyl isophthalate converts partially to alkyl isophthalic chloride due to the action of phosgene and/or hydrogen chloride in the phosgenation of toluylenediamine to toluylenediisocyanate. The process of the invention makes it possible to work up the phosgenation solvents contaminated with acid chloride following phosgenation of the toluylenediamine, the separation of the excess phosgene and the very volatile constituents as well as the toluylenediisocyanate. To this end, the solvent is mixed with the corresponding alcohol, the amount of which is governed by the degree of contamination of the solvent with acid chloride, and heated to the reaction temperature.

If the process is carried out with a superstoichiometric amount of alcohol, it is necessary to treat the solvents by distillation to effect removal of the excess alcohol. When effecting separation of the alcohol, the hydrogen chloride is concurrently also removed from the reaction mixture. If the process is carried out with a substoichiometric or stoichiometric alcohol concentration, purification of the end product by distillation is unnecessary, the solvents can be reused with the hydrogen chloride contained therein for subsequent phosgenation of TDA to TDI.

The purification of the diethyl isophthalate preferentially used as phosgenation solvent in industrial processes is preferably carried out at a temperature of from 160° to 240° C.

The invention is described below with reference to the following examples.

EXAMPLES

EXAMPLE 1

Two solutions were prepared. Solution 1 consisted of 67.5001 g of diethyl isophthalate, 15.0031 g of isophthalic dichloride and as internal standard 0.4005 g of eicosane. The second solution consisted of 67.5001 g of diethyl isophthalate and 16.9993g of ethanol. The two solutions were combined in an autoclave having a capacity of 300 mL, and nitrogen was forced in to create a pressure of 35 bar and the heating switched on. A temperature of 120° C. was reached after a period of 25 min. 10 minutes after this temperature had been reached, a sample was taken from the contents of the autoclave, in which sample no more isophthalic dichloride could be detected by gas chromatographic analyis. The concentration of ethyl isophthalate chloride was 0.00036 mol/kg as determined by gas chromatography. 30 minutes after the experimental temperataure had been reached a further sample was taken, in which no more ethyl isophthalate chloride could be detected by gas chromatography.

EXAMPLE 2

(Preparation of a solution of ethyl isophthalate chloride in diethyl isophthalate)

450.0 g of diethyl isophthalate, 100.05g of isophthalic dichloride and 67.90g of dehydrated ethanol were mixed together and stirred for 60 min at a temperature of 50° C. The resulting hydrogen chloride and the unconverted ethanol were then distilled off at a temperature of 20° C. in vacuo. There were obtained 555.52 g of a solution containing, as determined by gas chromatographic anylsis, 0.47 mol/kg of ethyl isophthalate chloride.

EXAMPLE 3

Equal volumes per unit of time of the solution prepared as described in Example 2 and of a solution of 14.57g of anhydrous ethanol in 539.95g of diethyl isophthalate were conveyed by means of two pumps, heated to 160° C., then mixed, and pumped through a tubular reactor heated at 160° C. and having a capacity of 42.4 mL. The mixture of the solutions resided in the reactor tube for 4 min. The pressure in the reactor was adjusted by a valve to 21 bar. The solution issuing from the tubular reactor was analyzed by gas chromatography. Analysis revealed a content of ethyl isophthalate chloride of only 0.079 mol/kg.

EXAMPLE 4

Example 3 was repeated except that the temperature was 200° C. The solution issuing from the tubular reactor was analyzed by gas chromatography. Analysis revealed a content of ethyl isophthalate chloride of only 0.008 mol/kg.

EXAMPLE 5

Equal volumes per unit of time of a solution prepared as described in Example 2, which contained 0.49 mol/kg of ethyl isophthalate chloride as determined by gas chromatographic analysis, and of a solution of 8,16g of anhydrous ethanol and 191.85 g of diethyl isophthalate were conveyed by means of two pumps, heated to 197° C., mixed, and pumped through a tubular reactor heated at 197° C. and having a capacity of 42,4 mL, in which the mixture of the solutions resided for 30min. The pressure in the reactor was adjusted to 17 bar by a valve. The solution issuing from the tubular reactor was analyzed by gas chromatography. No more isophthalate chloride was found.

We claim:

1. A method of converting a mixture of an alkyl carboxylate chloride and/or a carboxylic dichloride to a dialkyl carboxylate, the method comprising:

dissolving a reactant comprised of an alkyl carboxylate, a carboxylic dichloride or a mixture thereof, in a solvent consisting of a corresponding dialkyl carboxylate to form a reaction mixture;

reacting the reaction mixture with a corresponding alkanol at temperatures of from 60° to 300° C., under conditions such that substantially all of the hydrogen chloride generated as a result of the reaction remains in the reaction mixture; and maintaining such reaction for a time sufficient to achieve substantially complete conversion of the reactant to its corresponding dialkyl carboxylate.

2. The method of claim 1 wherein the reaction is maintained for a time of less than 4 hours.

3. A method as claimed in claim 1, wherein the reaction takes place at temperatures ranging from 100° to 250° C.

4. A method as claimed in claim 1, wherein the dialkyl carboxylate involved is, in particular, a dialkyl carboxylate of an aromatic dicarboxylic acid.

5. A method as claimed in claim 1 wherein the dialkyl carboxylate involved is a dialkyl isophthalate.

6. A method as claimed in claim 5, wherein the dialkyl isophthalate is diethyl isophthalate.

* * * * *